United States Patent [19]

Kopp et al.

[11] Patent Number: 4,496,491

[45] Date of Patent: Jan. 29, 1985

[54] AROMATIC DIISOCYANATES CONTAINING N,N-DISUBSTITUTED SULFONAMIDE GROUPS AND PROCESSES FOR THEIR PRODUCTION

[75] Inventors: Richard Kopp, Cologne; Gerhard Grögler, Leverkusen; Helmut Reiff, Leverkusen; Dieter Dieterich, Leverkusen, all of Fed. Rep. of Germany

[73] Assignee: Bayer Aktiengesellschaft, Leverkusen Bayerwerk, Fed. Rep. of Germany

[21] Appl. No.: 401,036

[22] Filed: Jul. 22, 1982

[30] Foreign Application Priority Data

Aug. 4, 1981 [DE] Fed. Rep. of Germany ....... 3130844

[51] Int. Cl.³ .......................................... C07C 119/048
[52] U.S. Cl. ......................... 260/453 AR; 260/239.6; 260/397.7 R; 260/453 AM; 260/453 P; 528/44; 548/518; 548/542
[58] Field of Search ................ 260/453 AR, 453 AM, 260/239.6, 397.7 R; 548/518, 542

[56] References Cited

U.S. PATENT DOCUMENTS 3,242,208  3/1966  Martin .................................. 260/552
3,576,872  4/1971  Singhal ................................ 260/562

FOREIGN PATENT DOCUMENTS 1117494  6/1968  United Kingdom .
1260881  1/1972  United Kingdom .

OTHER PUBLICATIONS

Abstract Netherlands, No. 7,105,350, 10/24/72.
Abstract Japanese, No. 73 16 502, 5/22/73.

*Primary Examiner*—Dolph H. Torrence
*Attorney, Agent, or Firm*—Gene Harsh; Joseph C. Gil; Lyndanne M. Whalen

[57] ABSTRACT

Diisocyanates corresponding to the formula

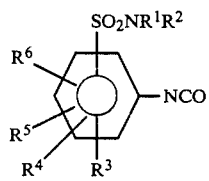

in which $R^1$, $R^2$, $R^3$, $R^4$, $R^5$ and $R^6$ (an isocyanate-containing radical) are as defined herein are made by several processes. These diisocyanates may be made by phosgenating the diamine in which the diisocyanate is based. They may also be produced by treating the bis-urethane of the tertiary alcohol corresponding to the diisocyanate with phosgene. Such diisocyanates may also be made by treating a specific type of bis-urea with hydrogen chloride. The diisocyanates corresponding to the above-given formula are particularly useful in the production of polyurethanes having good flame-proof and mechanical properties.

3 Claims, No Drawings

AROMATIC DIISOCYANATES CONTAINING N,N-DISUBSTITUTED SULFONAMIDE GROUPS AND PROCESSES FOR THEIR PRODUCTION

BACKGROUND OF THE INVENTION

The present invention relates to aromatic diisocyanates containing N,N-disubstituted sulfonamide groups, to processes for their production and to a process for the production of polyurethane plastics from these diisocyanates.

Aromatic monoisocyanates of which the aromatic nuclei are substituted by N,N-dialkyl sulfonamide groups are known (see for example Swiss Pat. No. 411,449; Belgian Pat. No. 734,235; U.S. Pat. No. 3,576,872; Netherlands Published Application No. 7,105,350; and Japanese Laid Open Application No. 7,316,502). Such monoisocyanates are used as coupling reagents in color photography, as intermediate products for resins, polymers, dyes, bleaching agents, pharmaceutical products, disinfectants and insecticides.

However, aromatic diisocyanates containing N,N-disubstituted sulfonamide groups on the aromatic nucleus are unknown. French Pat. No. 1,465,165 describes a process for the production of aromatic amines from isocyanates by the acid-catalyzed thermolysis of the corresponding secondary or tertiary alkyl carbamic acid esters. This French Patent also mentions that N-alkyl sulfonamido-aryl (di)isocyanates might be used as starting materials for the production of these alkyl carbamic acid esters. However, these diisocyanates are not illustrated in any of the Examples. Further, the availability of any such material is questionable because if the corresponding N-alkyl sulfonamido-aryl (di)amines are phosgenated to produce the isocyanates, the N-alkyl sulfonamide group is in danger of reacting in the secondary reaction represented by the folllowing equation:

$$R-SO_2-NH-R + COCl_2 \longrightarrow$$

$$R-SO_2-\underset{\underset{R}{|}}{N}-CO-Cl + HCl$$

SUMMARY OF THE INVENTION

It is an object of the present invention to provide aromatic diisocyanates containing N,N-disubstituted sulfonamide groups on the aromatic nucleus.

It is also an object of the present invention to provide a process for the production of aromatic diisocyanates containing N,N-disubstituted sulfonamide groups.

It is another object of the present invention to provide aromatic diisocyanates containing N,N-disubstituted sulfonamide groups on the aromatic nucleus which are physiologically safe and which are highly reactive with compounds containing isocyanate-reactive hydrogen atoms.

It is a further object of the present invention to provide a diisocyanate which when used in the production of polyurethane plastics improves the flameproof and mechanical properties of the polyurethane.

These and other objects which will be apparent to those skilled in the art are accomplished with diisocyanates corresponding to the formula

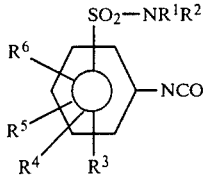

in which $R^1$, $R^2$, $R^3$, $R^4$, $R^5$ and $R^6$ are as defined below. These diisocyanates may be made by phosgenating the diamine on which the diisocyanate is based. They may also be produced by treating the bis-urethane of the tertiary alcohol corresponding to the diisocyanate with phosgene. The compounds of the present invention may also be made by treating a bis-urea corresponding to the diisocyanate and containing two specified structural units with hydrogen chloride to form ammonium salts as secondary amines are eliminated.

The compounds of the present invention are particularly useful as starting materials for the production of polyurethane plastics by the isocyanate polyaddition process because these diisocyanates and the polyurethanes produced from them appear to be physiologically acceptable substances. The aromatic diamines containing N,N-disubstituted sulfonamide groups on which they are based and which are formed during hydrolysis of the diisocyanates or polyurethanes do not show any activity in the Ames test according to Ames et al., Proc. nat. Acad. Sci. (USA), 70, 2281–2285 (1973) or Ames et al, Mutation Res. 31, 347–364 (1975) (verified for example with 1-(N,N-di-n-butyl-sulfonamido)-3,5-diamino-4-methyl benzene). These diisocyanates are also advantageous in that the reactivity of their isocyanate groups is greatly increased by the inductive effect of the disubstituted sulfonamide group, so that the new diisocyanates are particularly fast-reacting reactants for compounds containing isocyanate-reactive hydrogen atoms. Additionally, because of the increased content of oxygen, sulfur and nitrogen in these diisocyanates (compared to the conventional polyisocyanates of polyurethane chemistry), the flameproof properties of the polyurethane plastics produced with these diisocyanates are improved. Polyurethanes produced with the new diisocyanates also show improved mechanical properties, particularly at elevated temperatures.

DETAILED DESCRIPTION OF THE INVENTION

The present invention relates to diisocyanates corresponding to the general formula

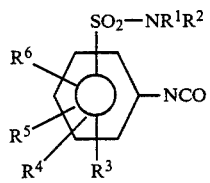

in which $R^1$ and $R^2$ (which may be the same or different) each represent an alkyl radical containing from 1 to 18 carbon atoms, an aryl radical containing from 6 to 10 carbon atoms, a cycloalkyl radical containing from 3 to 7 carbon atoms, an aralkyl radical containing from 7 to 15 carbon atoms or an alkaryl radical containing from 7 to 15 carbon atoms or, together with the nitrogen atom, form a 3-membered to 10-membered heterocyclic ring optionally containing further heteroatoms;

$R^3$, $R^4$ and $R^5$ (which may be the same or different) each represent hydrogen, an alkyl radical containing from 1 to 6 carbon atoms, an aryl radical containing from 6 to 10 carbon atoms, a cycloalkyl radical containing from 3 to 7 carbon atoms, an aralkyl radical containing from 7 to 15 carbon atoms, an alkaryl radical containing from 7 to 15 carbon atoms or a halogen atom; and $R^6$ represents an isocyanate group or a radical corresponding to the formula

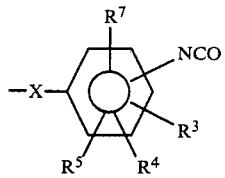

in which $R^7$ represents hydrogen or a radical corresponding to the formula

X represents a methylene group or a dimethylmethylene group; and $R^1$, $R^2$, $R^3$, $R^4$ and $R^5$ are as defined above.

The present invention also relates to a process for producing these diisocyanates in which the diamines on which the diisocyanates are based are phosgenated in accordance with techniques known to those in the art.

The present invention also relates to a process for producing these diisocyanates in which the bis-urethanes of tertiary alcohols corresponding to the diisocyanates are treated with phosgene.

The present invention also relates to a process for producing the diisocyanates of the present invention in which bis-ureas corresponding to the diisocyanates and containing 2 structural units corresponding to the formula

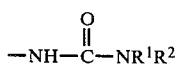

are treated with hydrogen chloride. Secondary amines corresponding to the formula

are eliminated with concurrent formation of the ammonium salts corresponding to the formula

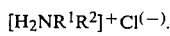

The present invention also relates to a process for the production of polyurethane plastics by the isocyanate polyaddition process from the diisocyanates of the present invention.

The preferred diisocyanates of the present invention are those corresponding to the above formula in which $R^1$ represents an alkyl radical containing from 1 to 6 carbon atoms, $R^2$ represents an alkyl radical containing from 1 to 18 carbon atoms, $R^3$ and $R^4$ represent hydrogen, $R^5$ represents hydrogen, an alkyl radical containing from 1 to 4 carbon atoms or chlorine and $R^6$ represents an isocyanate group.

In the production of the diisocyanates by phosgenation of the diamines on which they are based, the starting materials used are diamines corresponding to the formula

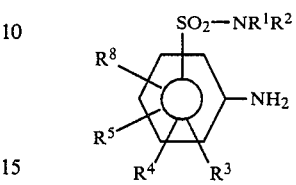

in which $R^1$, $R^2$, $R^3$, $R^4$, $R^5$, $R^7$ and X are as defined above and $R^8$ represents a radical corresponding to the formula

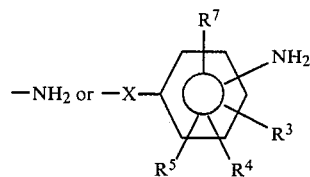

preferably a primary amino group.

The production of diamines such as these is described for example in German Patent Application No. P 30 12 800.8 (corresponding to European Patent Application No. 81 102 091.6 and to U.S. patent application Ser. No. 243,104 filed Dec. 3, 1981). These diamines are produced by converting alkali salts of the corresponding aromatic dinitrosulfonic acids into the corresponding sulfochlorides by known methods, subsequently converting the sulfochlorides into aromatic dinitrosulfonamides by reaction with secondary amines $HNR^1R^2$ in the presence of a base and then hydrogenating the aromatic dinitrosulfonamides thus formed to form the diamine.

Examples of diamines which may be obtained by this procedure and subsequently converted by phosgenation into the diisocyanates of the present invention include: 1-(N,N-di-n-butylsulfonamido)-3,5-diamino-4-methylbenzene, 1-(N-ethyl-N-phenylsulfonamido)-2,4-diaminobenzene, 1-(N,N-di-n-butylsulfonamido)-3-methyl-4,6-diaminobenzene, 1-(N-methyl-N-stearylsulfonamido)-3,5-diamino-4-methylbenzene and 1-[(2,5-diamino-4-methylphenyl)-sulfonyl]pyrrolidine.

Diamines which may be converted into the diisocyanates of the present invention by a simple phosgenation reaction may also be made by acylating an aromatic diamine (for example 4,4'-diamino-diphenylmethane) with acetic acid anhydride on the nitrogen atoms, subsequently sulfochlorinating both aromatic nuclei, converting the sulfochlorination product into the bis-sulfonamide by reaction with a secondary diamine and, finally, subjecting the bis-sulfonamide thus obtained to acid or alkaline hydrolysis to form the bis-sulfonamide diamine. Diamines such as 3,3'-bis-(N,N-dibutylsulfonamido)-4,4'-diaminodiphenyl methane may be made in this manner. Diamines of this type are described for example in J. Amer. Chem Soc. 74, (1952), pages 57 to 99 and in U.S. Pat. No. 3,639,342.

Phosgenation of the diamines may be carried out by the usual methods in one or two stages (cold-hot phosgenation) in the presence of suitable solvents (e.g., 1,2-dichloroethane, chlorobenzene or o-dichlorobenzene) at temperatures from about −20° C. to +200° C.

The diisocyanates of the present invention may also be produced by reacting the corresponding bis-urethanes of tertiary alcohols with phosgene. Suitable bis-urethanes are those corresponding to the formula

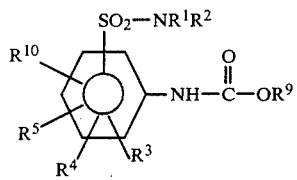

in which $R^1$, $R^2$, $R^3$, $R^4$ and $R^5$ are as defined above, $R^9$ represents a tertiary alkyl radical (preferably containing from 4 to 8 carbon atoms) and $R^{10}$ represents a radical corresponding to the formula

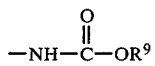

or to the formula

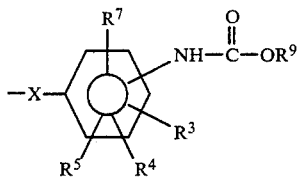

in which $R^3$, $R^4$, $R^5$, $R^7$, $R^9$ and X have the meanings defined above. This process for producing the diisocyanates of the present invention from bis-urethanes is analogous to that described in German Offenlegungsschrift No. 2,637,114 with the exception that secondary diamines corresponding to the formula $HNR^1R^2$ instead of the disclosed phenolates are reacted with the sulfochloride groups. The bis-urethanes to be treated with phosgene in this process of the present invention may thus be produced by converting aromatic diisocyanates free from sulfonamide groups into the corresponding isocyanato-sulfochlorides in accordance with techniques known to those in the art (see, for example, German Offenlegungsschrift No. 2,855,938), subsequently converting the isocyanate groups to urethanes with a tertiary alcohol (such as t-butanol) and subsequently reacting the sulfochloride groups with a secondary amine to form sulfonamide groups. This last step (which is not described in German Offenlegungsschrift No. 2,637,114) is preferably carried out in the presence of an alkaline-reacting compound in order to neutralize the hydrogen chloride formed. Secondary amines of the formula $HNR^1R^2$ suitable for use in this last step are, for example, dimethylamine, diethylamine, di-n-propylamine, diisopropylamine, the isomeric secondary butylamines or hexylamines, morpholine, pyrrolidine, N-methylstearylamine, N-methylaniline or N-ethylaniline. Suitable alkaline-reacting compounds are, for example, alkaline-earth or alkali hydroxides or even excess quantities of the above-mentioned secondary amines or tertiary amines (for example, pyridine or triethylamine).

In the above-described sulfonamide-forming reaction, the quantitative ratio between the reactants is generally such that the molar ratio of sulfochloride groups to secondary amine is between 1:1 and 1:2.5. It is particularly preferred to use the above-mentioned reactants in substantially equimolar quantities. As previously mentioned, the hydrogen chloride given off during the reaction may be bound either by excess amine $HNR^1R^2$ or by the addition of another base.

This reaction may be carried out by mixing all three components together at the same time or by initially introducing one or two components and then adding the remaining two components or the third component. It is therefore possible to first introduce the amine and then separately to run in the bis-urethane sulfochloride and the alkaline-reacting compound at the same time. Where substantially equimolar quantities of sulfochloride and amine are reacted, the best yields are generally obtained by initially introducing the sulfochloride in suspension in an apolar organic solvent (such as toluene) and then introducing the amine and the base at the same time.

It is, of course, possible to use other inert (i.e. polar) organic solvents in the above-described process. Appropriate solvents include tetrahydrofuran, dioxane, diethyl ether and acetone. The sulfonamide-forming reaction is generally carried out at temperatures in the range from −20° to 60° C. Sulfonamide formation is carried out with particular advantage in a one-pot process immediately after urethanization of the isocyanate groups without purification of the intermediate stage formed during the urethanization step.

Bis-urethanes containing sulfonamide groups may be treated with phosgene in the same manner as is described in German Offenlegungsschrift No. 2,637,114 to produce the diisocyanates of the present invention. More specifically, the bis-urethanes containing sulfonamide groups may be dissolved in a suitable solvent (such as 1,2-dichloroethane, chlorobenzene or o-dichlorobenzene) and the resulting solution treated with gaseous phosgene at around 0° C. to 100° C. Excess phosgene is then given off with an inert gas (such as nitrogen) and the solvent is evaporated off. The diisocyanate of the present invention accumulates as residue and may be purified either by distillation or by recrystallization.

The bis-urethanes useful in the above-described process may also be obtained from the corresponding diaminoaryl sulfonic acids by converting the diaminoaryl sulfonic acids with phosgene into the corresponding diisocyanato-arylsulfochlorides and processing these sulfochlorides in the manner described above.

In another process for producing the diisocyanates of the present invention, the corresponding N,N-disubstituted ureas are split by reacting the urea with hydrogen chloride. The secondary amine corresponding to the urea is eliminated and converted into the corresponding ammonium chloride. The bis-ureas used in this process correspond to the formula

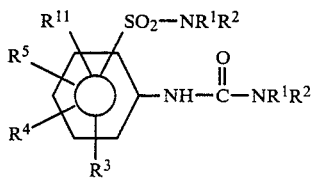

in which
the radicals $R^1$, $R^2$, $R^3$, $R^4$ and $R^5$ are as defined above, and
$R^{11}$ represents a radical corresponding to the formula $$-NH-CO-NR^1R^2$$

or to the formula

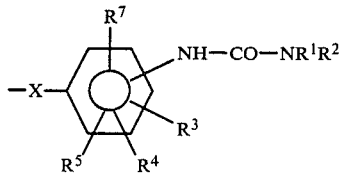

in which $R^1$, $R^2$, $R^3$, $R^4$, $R^5$, $R^7$ and X are as defined above.

Such bis-ureas may be formed by reacting the corresponding diisocyanato-aryl sulfochlorides with secondary amines $HNR^1R^2$ using at least 1 mole of the secondary amine for each mole of isocyanate groups and at least 2 moles of the secondary amine for each sulfochloride group. The function of the second mole of secondary diamine in the reaction of the sulfochloride groups with the secondary amine is neutralization of the hydrogen chloride given off.

The reaction of the diisocyanato-aryl sulfochlorides with the secondary diamines takes place spontaneously in a substantially quantitative yield. The reaction may be advantageously carried out in polar or apolar solvents of the type previously described at temperatures in the range of from 20° to 80° C. The solutions of the sulfonamide-group-containing bis-ureas which accumulate may then be immediately treated with hydrogen chloride. However, it is also possible to isolate the bis-ureas and to dissolve them in another solvent before they are treated with the hydrogen chloride. These bis-ureas are generally reacted with hydrogen chloride at temperatures in the range from 100° to 200° C. with thorough mixing of the bis-urea to be split. It is preferable that gaseous hydrogen chloride be used. The hydrogen chloride is preferably used in a molar excess. It is of particular advantage to introduce gaseous hydrogen chloride, (optionally together with an inert gas such as nitrogen or carbon dioxide) into the solution of the bis-urea at a temperature within the range of 100° to 200° C. In general, approximately 5 to 50 wt. % solutions of the bis-urea are used. It is particularly preferred to use solvents of the type which do not have boiling points below the reaction temperature. Particularly suitable solvents are xylene, toluene, monochlorobenzene, dichlorobenzene and trichlorobenzene. The hydrochloride of the split off secondary amine precipitates in these solvents and may be removed for example by filtration or by centrifugation. The solution of the diisocyanate remaining may then be worked up in the manner described above.

The diisocyanates of the present invention may be used instead of the usual diisocyanates for the production of polyurethane plastics by any of the methods known to those skilled in the art of polyurethane chemistry.

Having thus described our invention, the following Examples are given by way of illustration. The percentages given in the Examples represent percentages by weight unless otherwise indicated.

EXAMPLES

EXAMPLE 1

This Example illustrates production of diisocyanates by phosgenation of the corresponding diamines.

A solution or suspension of 1.12 mole of a diaminoaryl sulfonamide in 1300 ml of 1,2-dichloroethane was added over a period of 30 minutes at −10° to 0° C. to a solution of 495 g (5 moles) of phosgene in 1500 ml of 1,2-dichloroethane. The reaction solution was then refluxed for 3 hours while a constant stream of phosgene was passed through. Residues of phosgene were then removed by means of a stream of nitrogen over a period of 3 hours. The clear reaction solution was the concentrated in a rotary evaporator.

The NCO-content of the crude diisocyanate product (obtained in a substantially quantitative yield) was close to the theoretical value. The crude product could be purified by recrystallization or by distillation in an oil pump vacuum. The products thus prepared corresponded to the general formula

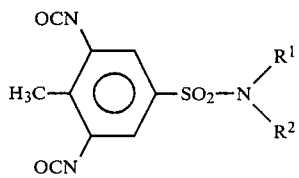

in which $R^1$ and $R^2$ were indicated in Table 1.

TABLE 1

| | | % NCO | | |
|---|---|---|---|---|
| $R^1$ | $R^2$ | (theoretical) | (actual) | M.p.t. |
| Ia | n-C$_4$H$_9$ n-C$_4$H$_9$ | 23.01 | 22.9 | 58–59° C. |
| Ib | CH$_3$ n-C$_{18}$H$_{37}$ | 16.2 | 15.1 | 67–69° C. |
| Ic | —(CH$_2$)$_4$—* | | 27.4 | 25.1 | 117–120° C. | or to the formula

OCN—⟨O⟩—SO$_2$—N—⟨O⟩  
         |       |
        NCO   C$_2$H$_5$

% NCO  24.5 (theoretical)
        23.1 (actual)
M.p.t.: 77–79° C.

*$R^1$ and $R^2$ combined.

$^1$H—NMR—, IR-spectra and elemental analyses confirmed these structures.

EXAMPLE 2

This Example illustrates production of 1-(N,N-di-n-butylsulfonamido)-2,4-diisocyanato-5-methylbenzene by phosgenation of the corresponding bis-urethane.

33.3 g (0.45 mole) of tertiary butanol were added dropwise over a period of 1 hour at room temperature to a solution of 54.5 g (0.2 mole) of 1-chlorosulfonyl-2,4-diisocyanato-5-methylbenzene and 0.05 g of tin(II)ethyl hexoate in 200 ml of ether. After stirring for 4 hours, the solids (minimal) were removed by filtration under suction and a solution of 54 g (0.42 mole) of dibutylamine in 50 ml of ether was added to the filtrate over a period of 1 hour. The dibutyl amine chloride which precipitated was filtered off and the filtrate was concentrated. The oily residue (80 g) of the bis-urethane solidified immediately to form a crystalline mass (M.P.t.=110°-115° C.).

| Analysis | C | H | N | S |
|---|---|---|---|---|
| Calculated | 58.5 | 8.4 | 8.2 | 6.2 |
| Observed | 58.3 | 8.3 | 8.2 | 6.6 |

Phosgene was introduced at room temperature into an approximately 20 wt. % solution of the bis-urethane in 1,2-dichloroethane and the reaction mixture gradually heated to 70° C. The excess phosgene was then removed with nitrogen and the dichloroethane evaporated off. The diisocyanate containing sulfonamide groups accumulated in the form of a crude oil having an NCO-content of 19.8% (calculated 23.0%) and solidified to form a solid having a melting point of 50° to 55° C.

EXAMPLE 3

This Example illustrates production of a diisocyanate according to the invention by treating the N,N-disubstituted urea on which the diisocyanate is based with hydrogen chloride.

(3a) Production of the bis-dimethylurea of 1-methyl-4-dimethylaminosulfonyl-2,6-diisocyanate 27.2 g (0.1 mole) of 4-chlorosulfonyl-2,6-diisocyanato-toluene were added all at once to a solution of 100 ml of 52% dimethylamine in water. The exothermic reaction was allowed to abate, and the reaction mixture was then stirred for 1 hour and freed from the excess amine by concentrating it to approximately one third of its original volume. Filtration under suction and drying left 27.4 g (74%) of the above bis-urea sulfonamide. It had a melting point of 237° to 238° C.

(3b) 4-dimethylaminosulfonyl-2,6-diisocyanato-toluene 7.4 g (0.02 moles) of the product of (3a) were dissolved in 100 ml of chlorobenzene. The solution was heated to reflux temperature, after which carbon dioxide and hydrogen chloride were simultaneously introduced. After 20 minutes the introduction of hydrogen chloride was stopped and, after blowing out with carbon dioxide for another 20 minutes, the reaction solution was cooled to room temperature. The dimethyl amine hydrochloride which precipitated was filtered under suction (86%). Removal of the chlorobenzene by distillation left 5.92 g of crude product (80%). The crude product was distilled in a high vacuum at a bath temperature of 200° to 230° C. (0.1 Torr). The melting point of the product was 111°-112° C. The calculated NCO content was 30.0% and the observed NCO content was 29.9%.

Infra-red and nuclear resonance spectra confirmed the structure.

EXAMPLE 4

In this Example the reaction velocities of diisocyanato-aryl sulfonamides with the corresponding aromatic diisocyanates are compared.

To determine relative reaction velocity, the following test was carried out:

0.004 mole of a diisocyanate in 100 ml of toluene were initially introduced into the reaction vessel at 23° C.±0.5° C. A solution of 0.08 mole of n-butanol in 100 ml of toluene was added at time t=0 min. The reduction in the NCO-content (a measure of the conversion) was then followed over the period "t". The reduction in the NCO-content as a function of time is shown in Table 2. The diisocyanates Ia and II prepared in Example 1 were compared with 2,4-diisocyanato-toluene ("2,4-T") and 2,6-diisocyanato-toluene ("2,6-T").

TABLE 2

| Com- | NCO-reduction as a function of time min. | | | | | | | |
|---|---|---|---|---|---|---|---|---|
| pound | 1 | 5 | 10 | 20 | 50 | 100 | 200 | 300 |
| Ia | 0.152 | 0.130 | 0.120 | 0.108 | 0.076 | 0.040 | 0 | |
| II | 0.082 | 0.0469 | 0.030 | 0.004 | 0 | | | |
| 2,4-T | 0.199 | 0.172 | 0.158 | 0.139 | 0.108 | 0.085 | 0.063 | 0.048 |
| 2,6-T | 0.197 | 0.181 | 0.174 | 0.165 | 0.148 | 0.127 | 0.095 | 0.072 |

EXAMPLE 5

In this Example, urethanes were produced by reacting diisocyanate Ia prepared in Example 1 and 2,6-diisocyanato-toluene with equimolar quantities of 1,4-butane diol. These reactions were studied by thermogravimetry and differential calorimetry.

Quantities of 0.028 mole of each of the above-mentioned diisocyanates were heated for 4 hours to 80° C. with 0.028 mole of 1,4-butane diol in 80 ml of chlorobenzene. The polyurethane thus obtained based on diisocyanate Ia had a melting point or melting range of 137°-150° C. The corresponding polyurethane based on the comparison diisocyanate had a melting range of 228°-235° C.

Thermogravimetric and differential-calorimetric studies were carried out with both polyurethanes. For the thermogravimetric study, the materials were heated under nitrogen at 20° K./min. (around 20° C. per minute) in a standard commercial thermobalance until the specimen had completely decomposed. The thermoanalytical studies were carried out under nitrogen at 15° to 150° C. using a standard commercial differential scanning calorimeter. The heating rate was again 20° K./min.

The results of these studies were as follows:

| | Ia | 2,6-T |
|---|---|---|
| Maximum in the differentiated thermogravimetric measurement (maximum decomposition rate) | 363° C. | 345° C. |
| Glass transition temperature as determined by differential calorimetry | 51° C. | 80° C. |

The compound of the diisocyanate Ia had a lower glass transition temperature and a greater heat stability (approximately 20° C. higher).

EXAMPLE 6

Elastomers produced with diisocyanate Ia from Example 1 and with 2,4-diisocyanato-toluene were compared. The prepolymers (A)-(D) described below were first prepared.

(A) 2000 g of a polyester obtained from adipic acid and ethylene glycol (MW 2000; OH-number 56) were heated to 70°-80° C. with 730 g of diisocyanate Ia and kept at that temperature until the NCO-content was 2.9-3.0 wt. %.

(B) Same NCO-prepolymer as (A), except that it was prepared with 348 g of 2,4-diisocyanato-toluene. The NCO-prepolymer had an NCO-content of 3.5 wt. %.

(C) The polyester of (A) was replaced by a polyether obtained by the addition of propylene oxide with propylene glycol (MW 2000; OH-number 56).

(D) The polyester of (B) was replaced by the polyether of (C).

300 g of the NCO-prepolymers (A)–(D) were briefly degassed in a water jet vacuum at 80° C. and thoroughly mixed for 30 seconds with molten 3,5-diamino-4-chlorobenzoic acid isobutyl ester. The quantity of diamine was gauged in such a way that the molar ratio of NCO to $NH_2$ was 1.1:1. The reaction mixture was poured into a mold heated to 100° C. and, after removal from the mold, was tempered for 24 hours at 110° C.

The mechanical properties of the elastomers thus produced are shown in Table 3. These results indicate that, by and large, the prepolymers produced with the diisocyanate of the present invention showed increased reactivity in comparison to the prior art diisocyanate. In addition, the elastomers produced with the diisocyanate of the present invention are characterized by greater softness for the same shock elasticity.

TABLE 3

| Prepolymer | Pouring time (mins.) | Lift time (mins.) | Modulus (kp/cm²) 100% DIN 53 504 | Modulus (kp/cm²) 300% DIN 53 504 | Breaking elongation (%) DIN 53 504 | Tear propagation resistance (kp/cm) DIN 53 515 | Shore A DIN 53 505 | Shore D DIN 53 505 | Shock elasticity (%) DIN 53 512 |
|---|---|---|---|---|---|---|---|---|---|
| A | 0.5 | 1 | 4.19 | 5.57 | 531 | 30.9 | 78 | 24 | 31 |
| B | 10 | 12 | 6.09 | 10.0 | 701 | 64.8 | 85 | 30 | 36 |
| C | 8 | 10 | — | — | 386 | 11.4 | 75 | 16 | 38 |
| D | 200 | 45 | 4.40 | 4.77 | 422 | 19.0 | 78 | 19 | 42 |

What is claimed is:

1. A diisocyanate corresponding to the general formula

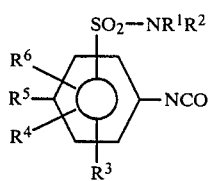

in which $R^1$ and $R^2$ (which may be the same or different) each represent an alkyl radical containing from 1 to 18 carbon atoms, an aryl radical containing from 6 to 10 carbon atoms, a cycloalkyl radical containing from 3 to 7 carbon atoms, an aralkyl radical containing from 7 to 15 carbon atoms or an alkaryl radical containing from 7 to 15 carbon atoms or, together with the nitrogen atom, form a 3-membered to 10-membered heterocyclic ring optionally containing further heteroatoms;

$R^3$, $R^4$ and $R^5$ (which may be the same or different) each represent hydrogen, an alkyl radical containing from 1 to 6 carbon atoms, an aryl radical containing from 6 to 10 carbon atoms, a cycloalkyl radical containing from 3 to 7 carbon atoms, an aralkyl radical containing from 7 to 15 carbon atoms, an alkaryl radical containing from 7 to 15 carbon atoms or a halogen atom; and $R^6$ represents an isocyanate group or a radical corresponding to the formula

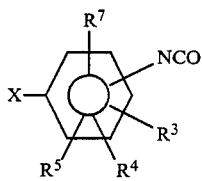

in which $R^7$ represents hydrogen or a radical corresponding to the formula $-SO_2NR^1R^2$ and X represents a methylene or a dimethyl methylene group.

2. The diisocyanate claimed in claim 1 in which $R^1$ represents an alkyl radical containing from 1 to 6 carbon atoms;

$R^2$ represents an alkyl radical containing from 1 to 18 carbon atoms;

$R^3$ and $R^4$ represent hydrogen;

$R^5$ represents hydrogen, an alkyl radical containing from 1 to 4 carbon atoms or chlorine; and $R^6$ represents an isocyanate group.

3. The diisocyanate claimed in claim 1 in which $R^1$ represents the radical n—$C_4H_9$, $R^2$ represents the radical n—$C_4H_9$, $R^3$ and $R^4$ represent hydrogen, $R^5$ represents a methyl group and $R^6$ represents an isocyanate group.

* * * * *